United States Patent [19]

Iwabuchi et al.

[11] Patent Number: 5,243,092
[45] Date of Patent: Sep. 7, 1993

[54] METHOD FOR PRODUCING 2,2-DIBROMO-2-NITROETHANOL

[75] Inventors: Koichi Iwabuchi; Hisatake Ogura; Tetsuo Horii, all of Shizuoka, Japan

[73] Assignee: K·I Chemical Industry Co., Ltd., Shizuoka, Japan

[21] Appl. No.: 915,665

[22] Filed: Jul. 21, 1992

[30] Foreign Application Priority Data

Sep. 11, 1991 [JP] Japan .................................. 3-258654
Oct. 31, 1991 [JP] Japan .................................. 3-313831

[51] Int. Cl.$^5$ .............................................. C07C 79/18
[52] U.S. Cl. ...................................... 568/713; 568/712
[58] Field of Search ................................ 568/712, 713

[56] References Cited

U.S. PATENT DOCUMENTS

| | | | |
|---|---|---|---|
| 3,658,921 | 4/1972 | Wessendorf | 568/712 |
| 4,233,245 | 11/1980 | Bourguignon et al. | 568/712 |
| 4,723,044 | 2/1988 | Watanabe et al. | 568/713 |
| 4,922,030 | 5/1990 | Nocito et al. | 568/713 |
| 5,075,510 | 12/1991 | Williams et al. | 568/712 |

FOREIGN PATENT DOCUMENTS

| | | | |
|---|---|---|---|
| 0340560 | 11/1989 | European Pat. Off. | 568/713 |
| 1-132549 | 5/1989 | Japan | 568/713 |

OTHER PUBLICATIONS

Chemische Berichte 57B, 2127–2128 (1924).
Chemische Berichte 56B, 611–620 (1923).

*Primary Examiner*—James H. Reamer
*Attorney, Agent, or Firm*—Birch, Stewart, Kolasch & Birch

[57] ABSTRACT

There is disclosed a method for producing,2,2-dibromo-2-nitroethanol. The method comprises first reacting tris(hydroxymethyl)nitromethane in aqueous solution with an alkali and then reacting the product of said first reaction with bromine.

8 Claims, No Drawings

METHOD FOR PRODUCING 2,2-DIBROMO-2-NITROETHANOL

FIELD OF THE INVENTION

The present invention relates to a method for producing 2,2-dibromo-2-nitroethanol in a high yield using tris(hydroxymethyl)nitromethane as a starting material. 2,2-Dibromo-2-nitroethanol is useful as an industrial bactericide and sulfide remover, as described, for example, in Japanese Patent Application (OPI) Nos. 134302/1990 and 135138/1990.

BACKGROUND OF THE INVENTION

To produce 2,2-dibromo-2-nitroethanol, for example, the following processes are known:

(1) A process wherein potassium hypobromite is reacted with 2-bromo-2-nitro-1,3-propanediol (Chemische Berichte 57B, 2127-2128 (1924)).

(2) A process wherein an alcoholate in alcoholic solution is reacted with 2-bromo-2-nitro-1,3-propanediol, the product is taken out and is suspended in dry ether, and a solution of bromine in chloroform is added to the suspension to carry out bromination (Chemische Berichte 56B, 611 to 620 (1923).

(3) A process wherein 1 mol of nitromethane is condensed with 1.5 mol or more of formaldehyde, followed by bromination with bromine (Japanese Patent Application (OPI) No. 289063/1986).

(4) A process wherein bromine is reacted with nitromethane in the presence of an alkali, followed by reaction with formaldehyde (Japanese Patent Application (OPI) No. 132549/1989).

However, these conventional manufacturing processes are attended by the problems given below and are not necessarily satisfactory for industrially practical processes.

First, the process (1) given above, wherein potassium hypobromite is reacted with 2-bromo-2-nitro-1,3-propanediol, gives a yield of 10.7% (given in the document), which is very low, and therefore the process is not suitable for industrial production at all.

The process (2), which uses 2-bromo-2-nitro-1,3-propanediol as a starting material, is complicated in procedure and gives a yield of 21% (given in the document), which is very low, and therefore the process is not suitable for industrial production.

With respect to the process (3), wherein nitromethane is condensed with formalin followed by bromination, when we carried out the replication of Example 1 shown in Japanese Patent Application (OPI) No. 289063/1986, in the oil fraction, the content of 2,2-dibromo-2-nitroethanol was 57.3 to 62.2%, and the yield was 36.6 to 37.2% based on the nitromethane, and therefore the process could not be satisfactory for industrial production in view of the quality and yield.

With respect to the process (4), wherein formalin is condensed with nitromethane bromide, when we carried out the replication of Example 1 of Japanese Patent Application (OPI) No. 132549/1989, little 2,2-dibromo-2-nitroethanol was formed, despite the description.

SUMMARY OF THE INVENTION

Therefore, an object of the present invention is to provide a method for obtaining 2,2-dibromo-2-nitroethanol in a high yield and in high purity by using relatively inexpensive and readily available compounds as raw materials.

Another object of the present invention is to provide a method for producing 2,2-dibromo-2-nitroethanol which is suitable for industrial application in view of the product quality and yield and of the safety in production.

Other and further objects, features, and advantages of the invention will appear more fully from the following description.

DETAILED DESCRIPTION OF THE INVENTION

The inventors have studied keenly to solve the above problems for commercialization, and have found that 2,2-dibromo-2-nitrothanol can be obtained in high yield by using tris(hydroxymethyl)nitromethane as a starting material, and by carrying out alkali decomposition in an aqueous medium, followed by bromination and pH adjustment, on which findings the present invention is based.

That is, the present invention provides a method for producing 2,2-dibromo-2-nitroethanol, which comprises reacting tris(hydroxymethyl)nitromethane in aqueous solution with an alkali and then reacting the product of the first reaction with bromine to form 2,2-dibromo-2nitroethanol.

It is assumed that all of the reactions in the method of the present invention are summarized in the following formula:

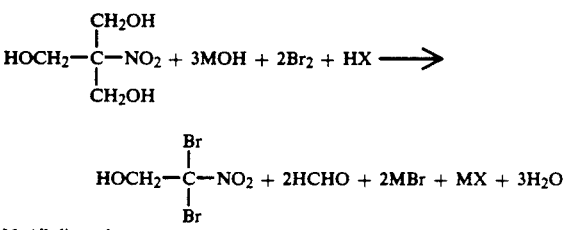

M: Alkali metal
HX: Inorganic acid

In the present invention, the first-step reaction is to form a salt of tris(hydroxymethyl)nitromethane with an alkali in aqueous solution. As the alkali, for example, sodium hydroxide, potassium hydroxide, lithium hydroxide, calcium hydroxide, magnesium hydroxide, and barium hydroxide can be mentioned, and preferably such a caustic alkali as sodium hydroxide or potassium hydroxide is used in view, for example, of the reactivity. The range of reaction temperature in the alkali treatment is usually from −10° to 60° C., preferably from 0° to 40° C., and the alkali is used preferably in an amount of 2.5 mol or more, more preferably 3.0 to 3.3 mol, for 1 mol of tris(hydroxymethyl) nitromethane. The reaction is usually completed soon after the addition of alkali.

The alkali is used to form an alkali salt of 2,2-dibromo-2-nitroethanol. If the amount of the alkali is not enough, in some cases the reaction will not proceed completely because of the shortage of alkali amount. The amount of alkali to be used is preferably 2.5 molar equivalents or more to 2,2-dibromo-2-nitroethane.

Water only or a water/alcohol mixture system can be used as the reaction medium, however a water-only system is more preferable in view of the solubility of the by-product, i.e., the metal bromide, and is also advantageous to avoid a risk of explosion or the like.

The second-step reaction is bromination. This can be carried out by adding bromine dropwise directly to the reaction product of &he first step without separating the product from the reaction mixture.

This bromination is carried out by using a brominating agent in a stoichiometric amount of 2.0 mol or more, preferably 2.0 to 2.3 mol, to 1 mol of tris(hydroxymethyl)nitromethane. The reaction temperature of bromination is preferably −10 to 10° C. The reaction comes to an end soon after the addition of brominating agent. After bromination, the reaction mixture is usually left standing to age for a time within 60 minutes, but this is not necessarily the case.

The pH of the reaction mixture after the bromination is adjusted to 7 or below, preferably to 3 or below, by using an acid, to finish the process. If the reaction mixture is left alkaline, the yield of 2,2-dibromo-2-nitroethanol is decreased because of the decomposition with alkali. Although there is no particular restriction on the acid used in the neutralization, it is preferable to use an inorganic acid, such as hydrochloric acid or sulfuric acid.

The thus obtained oil of 2,2-dibromo-2-nitroethanol and water layer are subjected to extraction with a solvent, such as toluene or chloroform, and the extract is purified by washing with water. Thus, highly pure 2,2-dibromo-2-nitroethanol can be obtained in a high yield with ease.

According to the method of the present invention, 2,2-dibromo-2-nitroethanol can be obtained in a high yield and in high purity by using tris(hydroxymethyl)nitromethane as a raw material, which is a readily available compound and is relatively inexpensive in cost. Further, since the reaction solvent is aqueous, the safety of the process is good. Therefore, the method of the present invention is quite suitable as an industrially practical method.

Now the present invention will be described in detail with reference to Examples.

ring. Then, 68.8 g (0.83 mol) of a 48% aqueous sodium hydroxide solution was added slowly dropwise from the dropping funnel while the temperature was kept at 5° to 15° C.

After completion of the dropping, 91.9 g (0.58 mol) of bromine was added to the reaction mixture dropwise while the temperature was kept at 0° to 5° C. After that the reaction mixture was left standing to age for 30 min with stirring, and then 35% hydrochloric acid was added dropwise thereto, to adjust the pH of the reaction mixture to 1. The reaction mixture was transferred into a separating funnel and was separated into an upper water layer and a lower oil layer, and each was collected separately. The water layer was extracted twice with 50 g each of toluene. The oil layer was dissolved in 150 g of toluene and then was washed with 50 g of water. The washings were further subjected to extraction with 25 g of toluene. All of the toluene layers were combined, and after the recovery of toluene under reduced pressure, the purified 2,2-dibromo-2-nitroethanol was obtained as a residue.

Examples 2 and 3 were conducted under the same reaction conditions as in Example 1, except that the molar ratios of sodium hydroxide and bromine were changed, and the respective results are shown in Table 1. The contents of 2,2-dibromo-2-nitroethanol in the oil and in the purified product were determined by gas chromatography using the internal standard method. The yield was based on tris(hydroxymethyl)nitromethane.

TABLE 1

| Example No. | Molar ratio | | | Oil | | | Purified product | | |
|---|---|---|---|---|---|---|---|---|---|
| | Tris-nitoro* | Sodium hydroxide | Bromine | Obtained amount (g) | Purity (%) | Yield (%) | Obtained amount (g) | Purity (%) | Yield (%) |
| 1 | 1 | 3.3 | 2.3 | 50.2 | 77.5 | 62.5 | 54.6 | 88.3 | 77.5 |
| 2 | 1 | 3.1 | 2.1 | 49.9 | 76.8 | 61.6 | 54.2 | 87.4 | 76.7 |
| 3 | 1 | 3.0 | 2.0 | 49.8 | 72.7 | 58.2 | 52.8 | 87.1 | 73.9 |

Note: *Tris(hydroxymethyl)nitromethane

From the results in Table 1, it can be understood that the yield of the purified product is as high as about 74% or more.

EXAMPLES 4 TO 5

Example 4 and 5 were conducted in the same manner as in Example 1, except that, instead of sodium hydroxide, potassium hydroxide in the same molar amount was used, thereby producing 2,2-dibromo-2-nitroethanol. The results are shown in Table 2.

TABLE 2

| Example No. | Molar ratio | | | Oil | | | Purified product | | |
|---|---|---|---|---|---|---|---|---|---|
| | Tris-nitoro* | Sodium hydroxide | Bromine | Obtained amount (g) | Purity (%) | Yield (%) | Obtained amount (g) | Purity (%) | Yield (%) |
| 4 | 1 | 3.3 | 2.3 | 49.9 | 73.6 | 59.0 | 53.1 | 85.9 | 73.3 |
| 5 | 1 | 3.0 | 2.0 | 47.1 | 72.3 | 54.7 | 50.1 | 87.1 | 70.1 |

Note: *Tris(hydroxymethyl)nitromethane

EXAMPLES 1 TO 3

Example 1 was conducted as follows:

A four-necked flask equipped with a thermometer, a reflux condenser, a dropping funnel and a stirrer was charged with 75.5 g (0.25 mol) of 50% aqueous solution of tris(hydroxymethyl)nitromethane and 75 g of water, and the mixture was cooled to below 15° C. with stir-

EXAMPLE 6

Example 6 was conducted in the same manner as in Example 1, except that the temperature at which the 8% aqueous sodium hydroxide solution was added was 25 to 35° C., thereby producing 2,2-dibromo-2-nitroethanol. The results are shown in Table 3.

TABLE 3

| Molar ratio | | | Oil | | | Purified product | | |
|---|---|---|---|---|---|---|---|---|
| Tris-nitro* | Sodium hydroxide | Bromine | Obtained amount (g) | Purity (%) | Yield (%) | Obtained amount (g) | Purity (%) | Yield (%) |
| 1 | 3.3 | 2.3 | 53.5 | 77.8 | 66.8 | 54.8 | 86.9 | 76.6 |

Note: *Tris(hydroxymethyl)nitromethane

COMPARATIVE EXAMPLE 1

A four-necked flask equipped with a reflux condenser, a dropping funnel, a thermometer and a stirrer was charged with 15.3 g (0.25 mol) of nitromethane, 37.5 g of water and 40.6 g (0.5 mol) of a 37% aqueous solution of formaldehyde. The mixed solution was cooled with stirring, and 80.0 g (0.5 mol) of a 25% aqueous sodium hydroxide solution was added dropwise while the temperature was kept at −5° to 0° C. After completion of the addition, the reaction mixture was left standing to age for 1 hour with stirring, and then 79.9 g (0.5 mol) of bromine was added dropwise while the temperature was kept at 0° to 5° C.

The reaction mixture was transferred into a separating funnel and was separated into oil and water layers. Each was collected separately, treated and analyzed similarly to Example 1. The obtained amount and the yield of the product are shown in Table 4. The reaction was repeated three times, each time yielding the same result. The yield was based on nitromethane.

TABLE 4

| | Oil | | | Purified product | | |
|---|---|---|---|---|---|---|
| | Obtained amount (g) | Purity (%) | Yield (%) | Obtained amount (g) | Purity (%) | Yield (%) |
| Comparative Example 1 | 40.3 | 57.3 | 37.1 | 40.4 | 73.8 | 47.9 |

As is shown in the above Table 4, the yield of purified product is lower as 47.9% than that described in Table 1.

COMPARATIVE EXAMPLE 2

A four-necked flask equipped with a thermometer, a reflux condenser, a dropping funnel and a stirrer was charged with 75.5 g (0.25 mol) of 50% aqueous solution of tris(hydroxymethyl)nitromethane and 75 g of water and the mixture was cooled to 15° C. or below with stirring. Separately, 91.9 g (0.58 mol) of bromine was added to 68.8 g (0 83 mol) of a 48% aqueous sodium hydroxide solution with cooling, to prepare a sodium hypobromite solution. This sodium hypobromite solution was placed in the dropping funnel and was added slowly dropwise to the previously prepared aqueous tris(hydroxymethyl)nitromethane solution while the temperature was kept at 0° to 5° C.

After completion of the addition, the reaction mixture was left standing for 30 min with stirring, and then 35% hydrochloric acid was added dropwise thereto, to adjust the pH to 1. When the reaction mixture was transferred to a separating funnel and was allowed to stand, there was no separation of an oil and the analysis of the reaction mixture did not detect 2,2-dibromo-2nitroethanol.

COMPARATIVE EXAMPLE 3

A four-necked flask equipped with a reflux condenser, a dropping funnel, a thermometer and a stirrer was charged with 75.5 g (0.25 mol) of 50% aqueous solution of tris(hydroxymethyl)nitromethane and 75 g of water and the mixture was cooled to below 15° C with stirring. Then, 439.9 g (0.83 mol) of a 20% aqueous sodium carbonate solution was added slowly dropwise while the temperature was kept at 5° to 15° C. After the completion of the addition, 91.9 g (0.58 mol) of bromine was slowly added dropwise while the temperature was kept at 0° to 5° C. The reaction mixture was left standing to age for 30 min with stirring, and then 35% hydrochloric acid was added dropwise thereto, to adjust the pH to 1. When the reaction mixture was transferred to a separating funnel and was allowed to stand, there was no separation of an oil and the analysis of the reaction mixture did not detect 2,2-dibromo-2-nitroethanol.

Having described our invention as related to the present embodiments, it is our intention that the invention not be limited by any of the details of, the description, unless otherwise specified, but rather that it be construed broadly within its spirit and scope as set out in the accompanying claims.

What we claim is:

1. A method for producing 2,2-dibromo-2-nitroethanol, which comprises first reacting tris(hydroxymethyl)nitromethane in aqueous solution with 2.5 mol or more of an alkyl per mold of tris(hydroxymethyl)nitromethane, and then reacting the product of said first reaction with bromine.

2. The method as claimed in claim 1, wherein the alkali to be used in the first reaction is selected from the group consisting of sodium hydroxide, potassium hydroxide, lithium hydroxide, calcium hydroxide, magnesium hydroxide, and barium hydroxide.

3. The method as claimed in claim 1, wherein the alkali to be used in the first reaction is sodium hydroxide or potassium hydroxide.

4. The method as claimed in claim 1, wherein the pH of the reaction mixture after the second reaction is adjusted to 7 or below.

5. The method as claimed in claim 1, wherein the first reaction is carried out at about −10° to about 60° C.

6. The method as claimed in claim 1, wherein the amount of bromine to be used in the second reaction is 2.0 mol or more per mol of tris(hydroxymethyl)nitromethane.

7. The method as claimed in claim 4, wherein the pH of the reaction mixture after the second reaction is adjusted to 3.0 or below.

8. The method as claimed in claim 1, wherein the amount of alkali to be used in the first reaction is 3.0 to 3.3 mol per mol of tris(hydroxymethyl)nitromethane.

* * * * *